(12) United States Patent  (10) Patent No.: US 8,213,013 B2
Zirk et al.  (45) Date of Patent: Jul. 3, 2012

(54) SUBSTANCE CONCENTRATION SENSOR AND PRODUCTION METHOD THEREFOR

(75) Inventors: Kai-Uwe Zirk, Dortmund (DE); Hans-Joachim Freitag, Erfurt (DE)

(73) Assignee: SES-Entwicklung GmbH, Dortmund (DE)

( * ) Notice: Subject to any disclaimer, the term of this patent is extended or adjusted under 35 U.S.C. 154(b) by 174 days.

(21) Appl. No.: 12/452,299

(22) PCT Filed: Jun. 7, 2008

(86) PCT No.: PCT/EP2008/004556
§ 371 (c)(1),
(2), (4) Date: Dec. 23, 2009

(87) PCT Pub. No.: WO2009/015723
PCT Pub. Date: Feb. 5, 2009

(65) Prior Publication Data
US 2010/0134798 A1    Jun. 3, 2010

(30) Foreign Application Priority Data
Jul. 5, 2007    (DE) .......................... 10 2007 031 284

(51) Int. Cl.
*G01N 21/00*    (2006.01)
(52) U.S. Cl. ....................................................... 356/436
(58) Field of Classification Search .................. None
See application file for complete search history.

(56) References Cited

U.S. PATENT DOCUMENTS 4,700,560 A * 10/1987 Hoffa et al. ..................... 73/1.04
7,352,464 B2 * 4/2008 Chen et al. ..................... 356/437

FOREIGN PATENT DOCUMENTS

| DE | 37 36 092 | 5/1989 |
| DE | 199 11 265 | 9/2000 |
| DE | 103 21 356 | 12/2004 |
| EP | 0 566 480 | 10/1993 |
| GB | 2 294 539 | 5/1996 |
| WO | WO 00/11453 | 3/2000 |

OTHER PUBLICATIONS

English translation of DE 199 11 265 A1.*
International Search Report.
Endo et al., "A needle-type optical enzyme sensor system for determining glucose levels in fish blood," Analytica Chimica Acta, Elsevier, Amsterdam, NL, vol. 573-574, Jul. 28, 2006, pp. 117-124, XP-022213545. (ISR).

* cited by examiner

*Primary Examiner* — Tu Nguyen
(74) *Attorney, Agent, or Firm* — Collard & Roe, P.C.

(57) ABSTRACT

The invention relates to a sensor for determining a concentration of a substance contained in a fluid-containing matrix, with a measurement chamber (5), a sender (3) for the emission of optical radiation (6) into the measurement chamber, and a receiver (4) for receiving optical radiation which has traversed the measurement chamber, wherein the measurement chamber is designed for bringing into the matrix and is filled with a specific fluid, and the wall (12, 13) is at least sectionally permeable to the diffusion of the substance. A control and evaluation circuit (7) is connected to the sender (3) and controls the sender (3), and is connected to the receiver (4) for selecting the receiver signals and determines, from the receiver signal, a measurement for the concentration of the substance in the matrix.

21 Claims, 3 Drawing Sheets

SUBSTANCE CONCENTRATION SENSOR AND PRODUCTION METHOD THEREFOR

CROSS REFERENCE TO RELATED APPLICATIONS

This application is the National Stage of PCT/EP2008/004556 filed on Jun. 7, 2008, which claims priority under 35 U.S.C. §119 of German Application No. 10 2007 031 284.0 filed on Jul. 5, 2007. The international application under PCT article 21(2) was not published in English.

OBJECT OF THE INVENTION

The present invention relates to a sensor for determining a concentration of a substance situated in a fluid matrix or a matrix containing fluid, having a measurement chamber, a transmitter for issuing optical radiation into the measurement chamber, and a receiver for receiving optical radiation that has passed through the measurement chamber, as well as to a production method for such a sensor. In particular, the invention relates to a sensor composed of a system that is present as a unit, having a transmitter and receiver integrated into the measurement chamber, as well as to preferred embodiments of it.

STATE OF THE ART

Measurement of substance concentrations is a technical task that is frequently found. It particularly encounters difficulties if the substance to be measured is present in a mixture with other substances. Such a matrix leads to the result that not only great sensitivity, but also the greatest possible selectivity of the measurement method is required for a precise measurement of concentration. Often, it is therefore not sufficient to make do with a single measurement, or very complicated selection mechanisms, such as gas chromatography, for example, have to be used. In this connection, the difficulty of the measurement task increases with the complexity of the matrix.

Very complex substance mixtures are naturally found in biological systems. Therefore measurement of a substance concentration in a biological matrix is one of the most complicated tasks.

Fundamentally, the measurement effort counteracts the possibilities of miniaturization of a measurement system. However, miniaturized substance sensors are of great interest, particularly for biological applications. It is known that it is vital in humans for some substances, such as glucose, saline solution, uric acid, amino acids, etc., to be present in a regulated concentration. In case of an illness, however, the biological control circuit can be derailed, so that the substance concentration of one or also multiple vital substances lies outside the physiologically normal range. In order to counteract such derailment by means of therapeutic measures, the value of the current concentration of the corresponding substance(s) must be known to the treating physician; therefore the concentration has to be measured, sometimes continuously.

For example, in the case of diabetes mellitus, caused by disturbed regulation of the metabolization of glucose in the body, the glucose level assumes overly high (too much sugar) or overly low (too little sugar) values. This leads to the irreversible death of nerve cells in the long term, and causes a number of pathological changes, primarily in the blood vessels. Resulting illnesses, such as blindness, loss of kidney function, cardiac infarction, high blood pressure as well as necrosis of limbs can be the result. For this reason, diabetes therapy requires that the glucose level be adjusted, as precisely and continuously as possible, to values in a medically acceptable range, by means of the administration of insulin or dextrose, for example. In this connection, the point in time and the amount of the insulin to be injected, or the need to consume food, are dependent on the current glucose concentration, as well as on the concentration progression over the course of the day. Thus, the glucose concentration is an example of a substance concentration in a complex matrix that should be monitored as continuously as possible, without any interruption in terms of time, and without complicated recurring adjustment measures. All therapies being carried out at this time, without exception, are dedicated to influencing the blood glucose level, and for this reason, most glucose concentration measurement devices also determine the glucose content in the blood. However, it is also known to use the interstitial fluid, since its glucose content follows that of the blood, proportionally, with only a slight time delay.

In DE 37 36 092 A1, a measurement device for polarimetric continuous glucose determination is disclosed for this purpose, whereby a measurement cuvette and a comparison cuvette are used, which are equipped, in part, with a membrane for ultrafiltration. However, it is not disclosed how the membrane is coupled with the cuvette, in technically very complicated manner. The concentration of the ultrafiltrate, in each instance, is obtained from the intensity difference of the measurement beam and the comparison beam.

In DE 19911265 C2, a device for measuring the glucose concentration of aqueous solutions that contain protein, particularly in interstitial tissue fluids, is described, in which a dialyzate is analyzed polarimetrically and spectrometrically at the same time. However, in the case of this device, the technical effort is tremendously great, here because of the parallel use of two measurement methods. The device described also allows the expectation of a large construction size. Furthermore, a dialysis membrane composed of plastic is mentioned for carrying out substance separation, but it is not disclosed in any detail how it is coupled to the optical measurement system, in technically very complicated manner.

Finally, DE 10321356 A1, which forms the type, discloses a method in which determination of the substance concentration of optically active components in media takes place, in that a measurement beam is passed from a radiation source to a coupling unit, coupled into a measurement chamber there, experiences a reversal in direction after having passed through the measurement chamber, on a reflection unit, passes through the measurement chamber again, and appears again at the coupling unit. In this method, the technical effort for the use of reflection and beam splitter units is very great. The question also remains open how determination of a substance in a matrix with other substances is supposed to take place in this method. If one wishes to determine the substance concentration in a biological tissue, the tissue or the interstitial fluid represents the matrix. Here, of course, a sensor that can be introduced directly into the tissue would be particularly advantageous, since then, continuous concentration monitoring of the selected substance is possible. This is not possible using the known devices of the type stated.

Task of the Invention

The invention is therefore based on the task of creating a measurement device of the type stated, as a sensor for specific, preferably continuous and absolute determination of the concentration of a substance in a fluid matrix or a matrix that contains fluid, preferably in biological tissue, whereby the sensor is supposed to be configured as compact as possible and preferably miniaturized.

Solution for the Task

This task is accomplished, according to the invention, with a sensor for determining a concentration of a substance situated in a fluid matrix or a matrix that contains fluid, having a measurement chamber, a transmitter for issuing optical radiation into the measurement chamber, and a receiver for receiving optical radiation that has passed through the measurement chamber, whereby the transmitter and receiver are used as part of the wall of the measurement chamber, in order to create a unit that is configured for introduction into the matrix, the measurement chamber is filled with a measurement medium and its wall is better diffusion-permeable for the substance than for matrix components, at least in certain sections, in order to balance out concentration differences of the substance between the measurement chamber and the matrix, and a control and evaluation circuit is provided, which is connected with the transmitter, in order to control it, and with the receiver in order to read out receiver signals, and which circuit determines a measure for the concentration of the substance in the matrix from the receiver signal.

MORE DETAILED EXPLANATION OF THE INVENTION

The sensor according to the invention therefore starts from the measurement principle of DE 10321356 A1 and significantly expands this, in that a separation of the substance contained in the matrix takes place by means of selective diffusion. In other words, the sensor implements a defined concentration equalization of the substance in the matrix and the measurement medium inside the measurement chamber, as well as, at the same time, an optical measurement in the measurement chamber, which leads to a compact unit overall. Furthermore, the sensor works without moving parts and can be configured as a simple puncture insertion sensor. In this regard, the invention particularly comprises one sensor.

As the result of the separation of the substance from the matrix that occurs in the sensor according to the invention, resulting from selective diffusion, the sensor solves the problem that exists in the state of the art, that of low specificity, from which a purely physical measurement method generally suffers. Because of the diffusion-related separation of the substance from the matrix, the sensor makes do with a simple optical measurement structure and can therefore be kept very compact. The wall therefore selects the substance from the matrix by means of its diffusion properties (substance separation properties), in that the substance is separated from other matrix components. In this connection, the substance separation can also take place by means of a size and/or shape selection, i.e. the wall only allows substances in a specific size range or a specific shape range of its molecules to pass through.

According to the invention, the sensor allows a simple optical measurement, by means of a defined substance separation, because the sensor possesses a preferably mechanically stable but in any case substance-diffusion-permeable wall, which brings about dynamic equalization of the concentration of the substance in the measurement medium with that in the matrix (e.g. intercellular fluid). An oblong housing that simultaneously accommodates the transmitter and receiver required for the optical measurement is preferred for building up the measurement chamber. The optical measurement method is significantly simplified by means of the substance-separating functionality of the sensor, and this allows compact, miniaturizable, and cost-advantageous implementation. In particular, substances that also act on the optical measurement method used, possibly to a much greater extent than the substance to be detected, can be prevented from getting into the measurement chamber by means of the diffusive substance separation.

The diffusion properties of the measurement chamber wall are preferably selected in such a manner that good diffusion and therefore good passage exist only for the substance to be measured, but not for other substances of the matrix to be measured. Therefore it is certainly also possible, within the scope of the invention, to predetermine or adjust the diffusion properties of the wall to match the matrix and the substance when designing the sensor.

The diffusion properties of the wall ensure the desired selectivity of the sensor, so that the optical measurement that takes place in the measurement chamber achieves a high specificity for the substance, without complicated optical structures being required. The electromagnetic, optical measurement beam generated by the transmitter (e.g. with wavelengths between 0.3 and 1.5 µm) passes through the measurement medium, i.e. the measurement chamber. It is possible to predetermine the type of measurement method (polarimetry or measurement of absorption or scattered light) by way of polarization states that can be predetermined by the transmitter (unpolarized, partly polarized, linearly polarized, elliptically polarized, or circularly polarized) and/or wavelength distribution of the measurement beam, and thus to adapt the sensor to one or more substances. After having passed through the measurement medium, the measurement beam impacts the receiver, which consists of one or preferably of at least two units that are independent of one another. In this way, a comprehensive measurement beam analysis is possible. If the receiver lies directly opposite the transmitter, with reference to the measurement chamber, only one passage through the fluid is necessary, and this leads to a streamlined structure.

The diffusion selection also reduces/prevents cross-influences of substances of the matrix, thereby making it possible to keep the structure compact. In particular, it is no longer absolutely necessary to reflect the measurement beam in the measurement chamber, as it is still described in DE 10321356 A1 for lengthening the measurement distance. Of course, this is nevertheless possible for a short structure.

The measurement chamber can preferably be formed by an oblong housing, e.g. a small tube, with the transmitter affixed at its one face end and the receiver affixed at its opposite face end. The cross-section of the oblong housing influences the diffusion equalization (diffusion time) and should therefore be selected to be as small as possible, in advantageous manner, thereby making it possible to implement a narrow housing, preferably with a diameter less than 3 mm. A sensor configured in this manner can then be implemented as an insertion puncture sensor, by means of suitable configuration of the housing, and has short diffusion times (adjustment times).

The measurement medium kept on hand in the measurement chamber is, of course, of importance for the diffusion properties of the substance through the wall. Also, the measurement chamber must, of course, be leak-proof for the measurement medium, in order to achieve long-lasting measuring ability. This can be implemented with particularly little effort if the transmitter and the receiver are glued into and/or onto the face ends of the housing, forming a seal. Then, the interior of the sensor can be configured to be leak-proof for the measurement medium, with few components.

For proper measurement, the measurement chamber should be filled with the measurement medium without any bubbles, in order to avoid disruptive reflections and scattering of the optical radiation, and/or to utilize the path of the radiation between transmitter and receiver as optimally as possible. Such filling can be implemented, in simple manner, in that the unfilled sensor is placed into an evacuated chamber into which the measurement medium is introduced. In this way, the sensor is also automatically filled with a suitable fluid.

With the aim of as compact a construction as possible, the control and evaluation circuit should be as close as possible to the sensor. For reasons of signal technology, it is advantageous to affix the circuit close to the receiver, since then even weak receiver signals can be read out well. Contacting to the transmitter, which is then situated at a distance, can take place on the outside of the housing if corresponding conductor tracks are provided. Of course, the electronics or part of it can also be disposed on the transmitter side.

Particularly simple laying of these conductor tracks is achieved if the housing has at least two grooves that run between the face sides, into which grooves one conductor track, in each instance, preferably configured as a thick-layer conductor, is introduced. Thick-layer technology for the production of the conductor tracks is a particularly good possibility if the wall has a porous material, at least in the diffusion-permeable sections, but particularly if the entire housing has a porous material, particularly a ceramic, silicon, plastic, glass, or metal.

In order to adjust the diffusion properties, it is practical to provide a carrier material that is not in and of itself selectively diffusion-permeable with a coating on the inside and/or outside, which coating imparts specific diffusion properties for the substance to the wall. This coating can be applied in a sol-gel method or a vapor deposition method or a deposition method, for example. This approach allows preparation of multiple housing parts in a long strand, from which the individual housings, e.g. tubules then only have to be cut off.

Measurement and Application Embodiments

Optical measurement in the measurement chamber is, of course, selected to match the substance to be detected and the measurement medium in the chamber. A possible optical method is a photometric method. Photometric methods are characterized, as compared with other analytical methods, by great sensitivity, simplicity, and the possibility of large series experiments under standardized conditions. Ultraviolet or visible radiation, for example, is used for a quantitative analysis by means of absorption photometry. This spectral range corresponds to changes in the energy of the valence electrons. However, use of the infrared spectral range, in which changes in the nuclear magnetic resonance energy of the molecules of the substance to be detected take place, is also possible.

However, only a small portion of the substances to be investigated demonstrates absorption bands in light (color) or in the ultraviolet range. In most cases, however, it is possible to transform the substance into a characteristically absorbing compound by means of suitable chemical reactions, and thus to determine its concentration. Since the introduction of photometrical measurement methods, well more than 1000 analysis methods have been described, all of which can fundamentally be applied here. The chemical reaction can be initiated in that the substance diffuses into the fluid of the chamber. For example, after appropriate processing, the following can be detected: ketone bodies, bilirubin, cholesterol, iron, bile acid, hemoglobin, uric acid, carbon monoxide, residual nitrogen in the blood, etc.

Another possible optical measurement is based on the polarimetric method, whereby in this connection, the substance to be detected must be optically active, something that applies to glucose, for example.

The optical measurement method in the sensor according to the invention can, of course, evaluate not only a polarization rotation, such as in the example of glucose, but also, as described above, an absorption, in other words a transmission weakening, as is possible in the case of lactose or uric acid, for example. Also, transmission weakening can be evaluated by means of scattering.

The measurement medium in the chamber, in other words the fluid, for example, should therefore sometimes be selected independent of the measurement method, the substance and/or the matrix. In particular, it can be selected in such a manner that it contains the substance to be measured in a standard concentration. The receiver signal then indicates deviations from the standard concentration. In the case of a biological tissue, a physiological saline solution or a glucose solution are possible fluids. Of course, the measurement medium can also be a gas or a gel.

An intensity change or rotation of the plane of vibration of the measurement beam while passing through the measurement medium is possible as a measurement variable detected by the optical measurement structure; this can take place by means of wavelength-selective or polarization-selective evaluation. Also, multiple beams can be evaluated at different wavelengths. For this purpose, it is preferred that the transmitter has at least one radiation source and an optical filter system or an imaging system or both. The imaging system ensures optimal passage of the radiation through the measurement chamber, and particularly adapts the optical radiation that is emitted by the radiation source to the cross-section and the length of the measurement chamber. For this purpose, it can comprise collimator optics, for example. The radiation source can be configured as a light-emitting diode, a laser diode, or a light-emitting diode array.

The filter system is coordinated with the optical effect to be evaluated, which can comprise, for example, broadband absorption, wavelength-selective absorption, polarization-dependent absorption, or polarization rotation. For this reason, it is practical if the filter system comprises a polarization filter and/or an interference filter and/or an edge filter.

In the simplest case, the receiver side comprises a photosensitive element for a measurement method. Particularly great measurement accuracy is achieved if quotient analysis and/or difference analysis takes place on the receiver side. For this reason, it is preferred if the receiver has at least two photosensitive elements and at least one optical filter system, which matches the filter system on the receiver side. Another possibility consists in utilizing two different optical effects with two photosensitive elements. The evaluation circuit determines the concentration of the substance from the signal change that is caused by the change in radiation brought about when passing through the measurement medium.

The approach according to the invention can be further refined if the measurement chamber includes at least one other closed chamber whose partition wall is diffusion-permeable for only part of the substances for which the wall of the measurement chamber is diffusion-permeable toward the outside. If one then also provides a transmitter and a receiver for this additional measurement chamber, an improved measurement can take place.

Production of the Sensor According to the Invention

The sensor according to the invention can be produced in very simple manner, as has already been explained above. Therefore, within the scope of the invention, a production method for a sensor of the type stated is also provided, in which method an oblong housing made of porous material, particularly ceramic, silicon, plastic, glass, or metal, is provided with a coating on the inside and/or outside, produced, for example, using a sol-gel method or a vapor deposition method or a deposition method, which coating imparts specific diffusion properties for a specific substance to the wall.

The sensor can be configured as an insertion puncture sensor, for example for measuring the glucose, urea, or lactose content in mammals, particularly in humans.

It is understood that the characteristics mentioned above and still to be explained below can be used not only in the combinations or embodiments indicated, but also in other combinations, with characteristics of other embodiments, or alone, without departing from the scope of the present invention.

DESCRIPTION OF FIG. 1-11

FIG. 1-11 shown in the drawings show:

EXPLANATION OF THE INVENTION USING FIGS. 1-11 AS EXAMPLES

Figure 1:
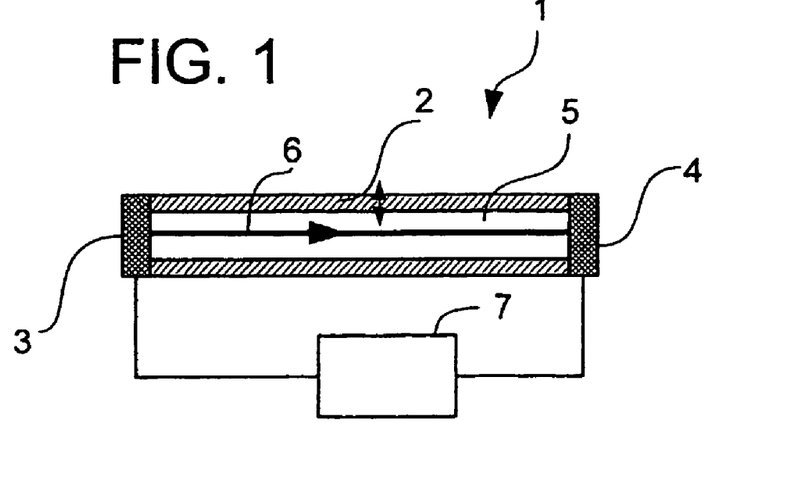
FIG. 1 a schematic representation of a sensor for measuring a substance concentration in a fluid, FIG. 2 a permeability curve for a wall of the sensor of FIG. 1, FIG. 3 a modified sensor, similar to that of FIG. 1, FIGS. 4 and 5 sensors similar to the one in FIG. 1, for measuring the substance concentration in the inter-cell or tissue fluid, FIG. 6 a sectional representation through the wall of the sensor of FIG. 4, FIG. 7 a schematic drawing relating to storage of the sensor of FIGS. 1 and 3 to 5, FIGS. 8 and 9 the sensor of FIGS. 1 and 3 to 5 with a housing, FIG. 10 another sensor variant, and FIG. 11 another sensor variant having two measurement chambers.

FIG. 1 schematically shows a longitudinal section through a sensor 1 for specific, continuous, and absolute determination of the concentration of a substance in a matrix, for example the glucose concentration in a biological tissue. In this connection, the sensor 1 utilizes an optical measurement principle, as will still be explained. It has a mechanically stable housing 2 that is configured as a tubule in the exemplary embodiment. At the face sides of the housing 2, there are a transmitter 3 and a receiver 4. The housing 2 is thereby sealed in fluid-tight manner at its face sides, since the transmitter 3 and the receiver 4 are correspondingly connected with, e.g. glued to the face sides. In the schematic representation of FIG. 1, it can be seen that in the embodiments selected here, the two components are glued onto the face sides. Of course, it is also possible, as will still be explained elsewhere, to glue the components into the tubule at the face-side ends. Thus, a measurement chamber 5 is formed in the housing.

The measurement chamber 5 closed off in this manner is filled with a known fluid (measurement medium). The wall of the housing 2 allows diffusive substance equalization between the surrounded matrix and the measurement medium in the measurement chamber 5, in bi-directional and substance-selective manner. In this connection, the selection is selected in such a manner that if at all possible, only the substance to be detected can diffuse through the wall of the housing 2, or at least has a diffusion coefficient that is higher by one order of magnitude than that of the remaining substances of the matrix, to the extent that these substances act on the measurement effect, which will still be explained. The diffusion route is illustrated with a double arrow in FIG. 1 and in the other FIGS. 3 to 5.

An optical beam 6 emitted by the transmitter 3 can be detected directly by the receiver 4 after it has passed through the measurement medium and possibly interacted with substances contained in it. In the embodiment of FIG. 1, the weakening in intensity of the optical beam 6 is dependent on the absorption behavior of the substance in the fluid. The absorption is linked, in known manner, with the substance concentration, so that a direct conclusion concerning the substance concentration is possible based on the intensity of the optical beam at the receiver 4 and thus on the value of the receiver signal. The method of construction of FIG. 1 is therefore particularly suitable for substances that influence absorption.

Transmitter 3 and receiver 4 are both connected with control electronics 7 that turn the transmitter 3 on, on the one hand, and read out the receiver 4, on the other hand. A simple two-point calibration, for example, is possible for an absolute determination of the substance concentration with the sensor. For this purpose, the value of the receiver 4 is read out at two known substance concentrations, in each instance. Preferably, zero and the normal solution are selected as the concentration. From these two measurement values, a linear sensor characteristic line is obtained, as a good approximation, for the absolute measurement of the substance concentration. Before the sensor 1 is inserted into the matrix, for example before it is introduced into biological tissue, a recalibration is also possible, in simple manner, if the interaction of the radiation with the fluid before first use is simultaneously known, so that the subsequent measurement takes place as an absolute measurement, since the deviation from the preceding calibration is detected.

Figure 2:
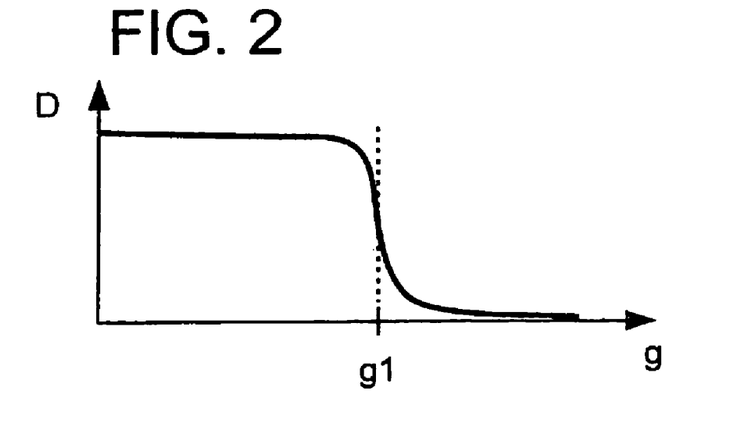

FIG. 2 illustrates the effect of diffusion. There, the permeability D is plotted as a function of the size g of a substance. The wall of the housing 2 allows substances having a size smaller than the size g1 to enter into the interior of the measurement chamber 5, i.e. the housing 2, whereas substances that are larger are not allowed to pass through. An example of a value for the size g1 is 30 kDalton, for example. At a size selection value generated in this way, by means of treatment and configuration of the wall, glucose, for example, can diffuse into the fluid 5, but larger substances such as proteins, for example, which would demonstrate a greater effect with regard to the measurement effect that will still be explained, would not penetrate into the measurement medium. In addition to the dynamic and defined substance selection brought about in this manner, the housing 2 here also serves as a mechanical connecting element between the transmitter 3 and receiver 4 provided for the optical measurement; they are attached at the ends of the housing and thus are part of the wall of the measurement chamber 5.

Figure 3:
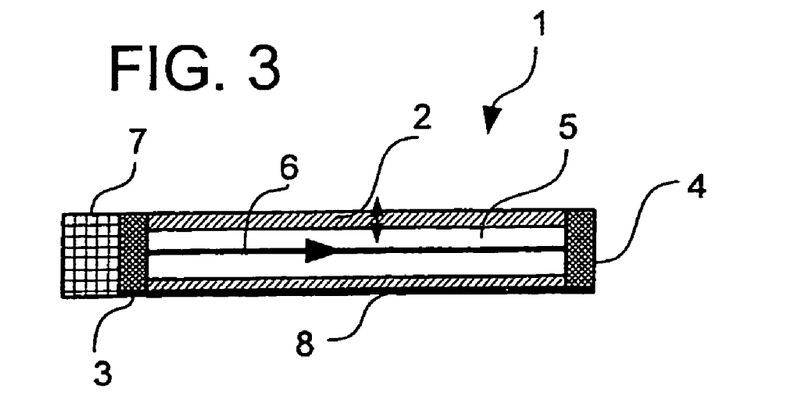

FIG. 3 shows a modified construction of FIG. 1. The only difference is that for miniaturization, the electronics 7 are set onto the face side, as an extension of the oblong housing 2. In the construction shown, the electronics 7 are situated on the transmitter-side face side. In this connection, the electronics 7 preferably continue the outline of the housing 2 or project only slightly beyond it. However, now electrical contacting to the other face side, on which the receiver 4 sits in the construction of FIG. 3, is required. For this purpose, at least two conductor tracks 8 are laid along the housing 2, which run on the outer wall, in the wall, or along the inner wall.

Figure 4:
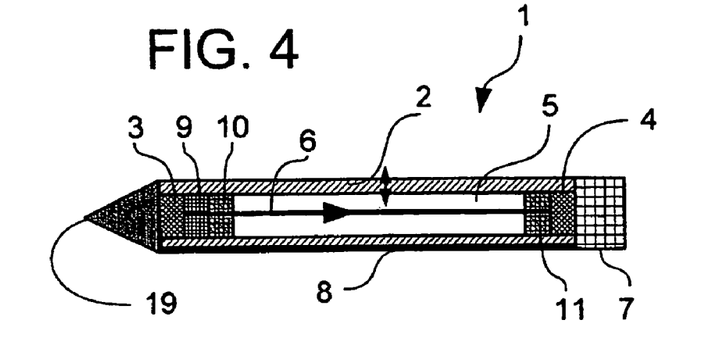

FIG. 4 shows a method of construction that is similar to that of FIG. 3, but the electronics 7 are now situated on the receiver side. Furthermore, transmitter 3 and receiver 4 are now no longer glued onto the face surfaces of the tubule, but rather glued into the oblong housing 2 on the face sides. For the remainder, the sensor 1 is configured as an insertion puncture sensor here, in that it has a point 19 on the face side.

Furthermore, it can also be seen that the transmitter 3 is additionally supplemented with an imaging system 9 and a filter system 10, which lie ahead of the radiation source. The imaging system 9 can be configured as collimator optics, for example, and ensures that the optical radiation 6 is emitted to the receiver 4 in as homogeneously distributed and directed manner as possible. The filter system 10 can be a polarization filter, an interference filter, or an edge filter, for example. The configuration of the optical filter system 10 is determined by the type of measurement method. For example, in the case of a polarimetric measurement method the filter system 10 will have a polarization filter. An optical receiver filter system 11 that matches the optical filter system 10 on the transmitter side is disposed in the receiver 4. Of course, both filter systems can have not just a single filter type, but also a combination of different filters.

Figure 5:
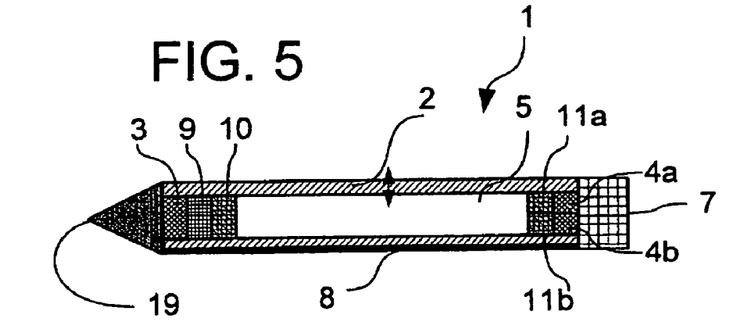

FIG. 5 shows a further development of the sensor 1 of FIG. 4. Here, two receiver units 4a and 4b that are independent of one another are now provided, which allow evaluation of the optical measurement beam according to two criteria, independent of one another. For example, a polarimetric rotation of also wavelength-dependent absorption, or both at the same time, can be evaluated. The filter systems 11a, 11b that precede the receivers 4a, 4b are, of course, coordinated with the measurement method(s), in each instance. The structure of FIG. 5 allows a polarimetric difference measurement, for example, if two polarization filters are used, for example, whose polarization direction is rotated by 90° relative to one another and by 45° relative to the transmitter polarization filter 10, in each instance.

Figure 6:
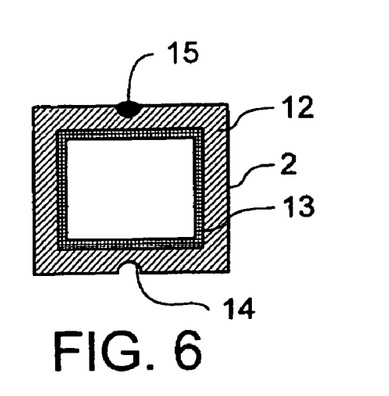

An example for electrical contacting by means of conductor tracks 8 along the housing 2, as shown in FIGS. 3 to 5, is illustrated in FIG. 6, which shows a cross-section through the oblong housing 2. As can be seen, the oblong housing 2 and thus the measurement chamber 5 have a rectangular cross-section. On the outer surface, two grooves 14 are placed, which run along the longitudinal axis of the housing and thus essentially parallel to the direction of the optical beam 6 (perpendicular to the plane of the drawing in FIG. 6). Thick-layer conductors 15 are introduced into the grooves 14 (for better clarity, no thick-layer conductor is shown in the lower groove). The groove 14 facilitates production of the thick-layer conductor 15, since the conductive paste can simply be applied with a squeegee; furthermore, it protects the conductor 15 from mechanical damage.

Furthermore, the cross-sectional representation of FIG. 6 shows a two-part structure of the housing 2, composed of carrier body 12 and a coating 13 (which lies on the inside here). The coating 13 (for example composed of titanium oxide materials) sets the desired diffusion properties of the wall of the housing 2. The carrier body is preferably composed of a porous material that does not have any selective diffusion properties for the substance to be detected, but rather is as neutral as possible with regard to its diffusion properties. Porous ceramic, silicon, plastic, glass or metal are possible materials. The inner wall of the square cross-section (of course other cross-sections such as rectangular, polygonal, round, etc., are also possible) is provided with a coating 13 (for example a carbon or ceramic coating) using a sol-gel method (other coating methods are also possible), which coating has a thickness of only a few nanometers or micrometers. The coating 13 is selected to be diffusion-selective, i.e. it has a substance-dependent diffusion coefficient that significantly promotes the diffusion of the substance to be detected. The coating represents a fine-mesh filter that blocks out all substances that are larger than the substance to be detected (glucose, for example). The substance to be detected can therefore diffuse through the composite structure of the wall of the measurement chamber 5 very much better than such other substances. Thus, only the substance to be detected diffuses into and out of the fluid, so that a change in the composition takes place directly and only by means of the substance to be detected.

Figure 7:
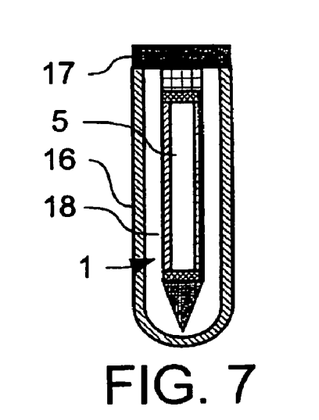

According to FIG. 7, the sensor 1 hangs on a lid 17 of a storage housing 16. It is, of course, of some importance for the sensor 1 that filling with the measurement medium 5 is complete, in other words free of bubbles, and as permanent as possible. Thus, of course, it should be avoided that in the case of a fluid as the measurement medium, this fluid runs or evaporates out of the interior of the housing. For this purpose, a storage housing 16 is therefore provided, into which the sensor 1 is placed and hangs on a lid, according to FIG. 7. The storage housing 16 is completely filled with fluid 18, whereby this is preferably precisely the same fluid that is also found in the interior of the sensor 1. At the same time, calibration of the sensor 1 can take place in the storage housing 16.

Figures 8, 9:
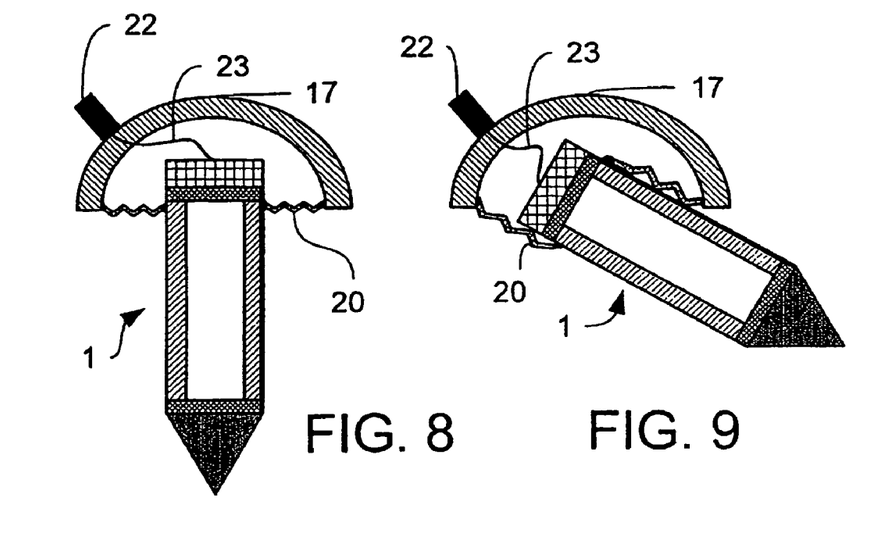

FIGS. 8 and 9 show, in a preferred further development, that the lid 17 can be configured in such a manner that it serves as a housing cap on the corresponding face side of the sensor 1, and remains on it even when the sensor is in use. Here, the lid 17 is configured as a half-round cap that is connected with the sensor 1 by way of elastic connection crosspieces or membranes 20. The cap furthermore has a signal transmission means 22, for example in the form of a radio transmitter or a plug that is connected with electronics 7 through the cap, by way of a cable 23, so that the lid 17 also makes the connection means for the sensor 1 available. The elastic connection by way of the membranes 20 brings about the result that the sensor 1, which is configured as an insertion puncture sensor, can also be inserted at a slant, so that the longitudinal axis of the sensor 1 can be pivoted relative to the lid 17, without transferring disruptive forces to the sensor 1. Of course, the lid 17 can also be configured at a slant. Such mechanical uncoupling between lid 17 and housing 2 clearly increases the mechanical stability when the sensor is used as an insertion puncture sensor. The sensor 1 is configured as an insertion puncture sensor by means of the tip 19 provided on the face side, and can be inserted into suitable tissue (for example subcutaneous fatty tissue). There, it can remain over an extended period of time (several days) and measure continuously.

Figure 10:
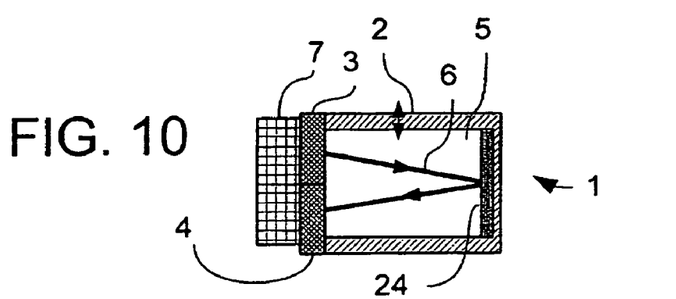

FIG. 10 shows an alternative construction of the sensor 1, in which a reflection layer 24 is disposed in the measurement chamber, on the face side of the housing 2, and transmitter 3 as well as receiver 4 lie on the opposite face side of the housing 2. The optical radiation 6 is therefore reflected on the reflection layer 24. This method of construction leads to a shorter sensor 1, at the same optical path length, and, at the same time, contacting of transmitter 3 and receiver 4 by the electronics 7 is possible in simple manner, since both elements to be contacted lie on the same side of the housing 2.

Figure 11:
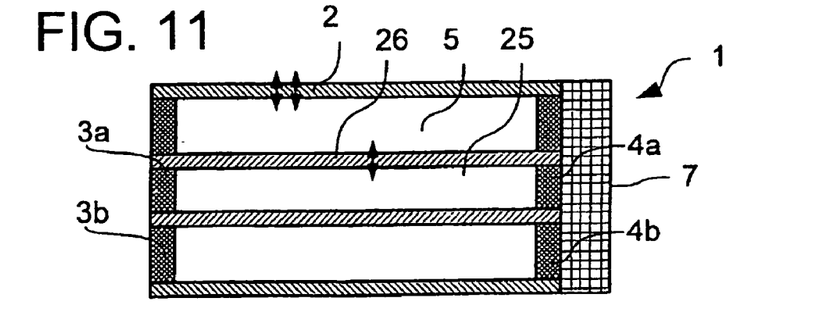

As is shown as an example in FIG. 11, the sensor principle shown can, of course, also be carried out with two sensors 1 for forming a quotient and/or difference, or a dual-chamber sensor whose chamber walls have different diffusion properties. Here, at least one additional chamber 25, which is delimited from the measurement chamber 5 by means of one or more inner walls 26, is provided in the measurement chamber 5. The diffusion properties of these inner walls differ from the diffusion properties of the (outer) wall of the measurement chamber 5. The inner wall 26 allows only part of these substances that can diffuse through the (outer) wall of the housing 2 to pass through. FIG. 11 illustrates this different diffusion behavior with two double arrows for the wall of the housing 2 and only one double arrow for the wall 26. This structure brings about the result that only part of the substances that are in the measurement chamber 5 can also diffuse into the inner, additional measurement chamber 25. A more precise measurement method is the result.

Of course, a transmitter 3a and 3b, respectively, is provided both for the (outer) measurement chamber 5 and for the (inner) measurement chamber 25, and a receiver 4a and 4b, respectively, detects the radiation that has passed through the chamber, in each instance. The placement of the chambers can be selected as desired, within the scope of what is technically possible, as long as care is taken to ensure that only part of those substances that can diffuse into the (outer) measurement chamber 5 can diffuse into the (inner) additional measurement chamber 25. For example, the measurement chamber 5 can contain an inner chamber 25 having a smaller cross-section, which is suitably supported in the measurement chamber 5 (for example on the face sides). Also, it is possible to affix two partition walls in the measurement chamber 5, in sealed manner, which walls delimit the additional chamber 25.

In a simplified construction, a common transmitter 3 can be used for both chambers, which then extends over the face sides of both chambers, for example. If one uses a receiver with spatial resolution, for example, this concept can also be pursued on the receiver side. The representation of FIG. 11 should be understood merely as an example in this regard, and should not be interpreted as being restrictive. Also, in FIG. 11, for the sake of simplicity, the electrical contacting from the control device 7 to the transmitter or the transmitters is not shown. This can run along the outer wall and/or on the partition wall.

In this regard, the invention particularly relates to a sensor for determining the concentration of a substance found in a fluid matrix or matrix that contains fluid, having a measurement chamber 5, a transmitter 3 for issuing optical radiation 6 into the measurement chamber 5, and a receiver 4 for receiving optical radiation 6 that has passed through the measurement chamber, which sensor is characterized in that transmitter 3 and receiver 4 form a part of the face side or the opposite side of the measurement chamber 5, in each instance, and this chamber is selectively diffusion-permeable for the substance to be measured, at least in certain sections, whereby this unit formed from 3, 4, and 5 is formed, at least in the diffusion-permeable sections, from a porous material 12, selected from among silicon, glass, ceramic, plastic, metal, particularly ceramic, and the sensor furthermore comprises control and evaluation electronics 7, which are connected with the transmitter 3 to turn it on, and the receiver 4 to read out receiver signals, and which determine a measure for the concentration of the substance in the matrix from the receiver signal.

Preferably, the porous material 12 of the unit 3, 4, and 5 has a diffusion-imparting coating 13, particularly composed of titanium dioxide materials, on the inside and/or outside.

The invention claimed is:

1. A sensor for determining a concentration of a first substance found in a matrix, the matrix being a fluid matrix or a fluid-containing matrix, the sensor having:
a measurement chamber,
a transmitter for issuing optical radiation into the measurement chamber,
a receiver for receiving optical radiation after the optical radiation has passed through the measurement chamber, and
a control and evaluation circuit connected with the transmitter to turn the transmitter on, and connected with the receiver to read out a signal from the receiver,
wherein the transmitter and the receiver are part of a wall of the measurement chamber, so that a unit formed in this manner is configured for introduction into the matrix,
wherein the measurement chamber is filled with a measurement medium,
wherein the wall of the measurement chamber is better diffusion-permeable for the first substance, at least in certain sections, than for remaining substances of the matrix, in order to balance out concentration differences of the first substance between the measurement medium and the matrix, and thus to separate the first substance from the remaining substances of the matrix, and
wherein the control and evaluation circuit determines the concentration of the first substance in the matrix from the signal from the receiver.

2. The sensor according to claim 1, wherein the measurement chamber is formed by an oblong housing,
wherein the transmitter is affixed on a first face side of the oblong housing, and
wherein the receiver is affixed on a second face side of the oblong housing, the second face side being opposite from the first face side.

3. The sensor according to claim 2, wherein the oblong housing is tubular and has a diameter of less than 3 mm.

4. The sensor according to claim 2, wherein the transmitter and the receiver are glued to the first and second face sides of the oblong housing, respectively, to be tightly fixed in place.

5. The sensor according to claim 2, further comprising conductor tracks on an outside of the oblong housing,
wherein, by way of the conductor tracks, the control and evaluation circuit is connected with at least one of the transmitter and the receiver.

6. The sensor according to claim 2, wherein the oblong housing has at least two grooves running between the first and second face sides,
wherein a first conductor track is introduced into a first groove of the at least two grooves, and
wherein a second conductor track is introduced into a second groove of the at least two grooves.

7. The sensor according to claim 2, wherein the oblong housing is configured as an insertion puncture sensor such that the oblong housing has a tip at one end of the oblong housing.

8. The sensor according to claim 1, wherein the transmitter has a radiation source and at least one of an imaging system and an optical filter system.

9. The sensor according to claim 8, wherein the radiation source comprises a light-emitting diode, laser diode, or light-emitting diode array.

10. The sensor according to claim 8, wherein the transmitter has an imaging system comprising collimator optics.

11. The sensor according to claim 8, wherein the transmitter has an optical filter system comprising at least one member selected from the group consisting of a polarization filter, an interference filter, and an edge filter.

12. The sensor according to claim 8, wherein the control and evaluation circuit determines at least one of a polarization rotation and an intensity change of the radiation as the radiation passes through the measurement chamber filled with the measurement medium, the control and evaluation circuit deriving the concentration of the first substance via the determination.

13. The sensor according to claim 1, wherein the receiver has two photosensitive elements and at least one optical filter system.

14. The sensor according to claim 1, wherein the measurement medium is a physiological saline solution or glucose solution, and
wherein the matrix is a biological tissue.

15. The sensor according to claim 1, wherein the wall brings about at least one of a size selection and a shape selection, so that better diffusion permeability for substances having a certain size or molecular shape exists.

16. The sensor according to claim 1, wherein the wall has a porous material comprising ceramic, silicon, plastic, glass, or metal, at least in diffusion-permeable sections,
wherein the porous material is provided with a coating on at least one of an inside of the porous material and an outside of the porous material, and
wherein the coating imparts specific diffusion properties for the first substance relative to the wall.

17. The sensor according to claim 1, further comprising:
a sealed chamber having at least one partition wall delimiting the sealed chamber from the measurement chamber,
a sealed-chamber transmitter on the at least one partition wall, and
a sealed-chamber receiver on the at least one partition wall
wherein at least one of the transmitter and the sealed-chamber transmitter can issue optical radiation into the sealed chamber,
wherein at least one of the receiver and the sealed-chamber receiver can receive optical radiation after the optical radiation has passed through the sealed chamber,
wherein the wall of the measurement chamber is diffusion-permeable for at least two substances, and
wherein the at least one partition wall is diffusion-permeable for only part of the at least two substances.

18. A production method for producing a sensor, the production method comprising steps of:
providing a unit comprising:
a measurement chamber formed by an oblong housing, being filled with a measurement medium, and having a wall;
a transmitter for issuing optical radiation into the measurement chamber; and
a receiver for receiving optical radiation after the optical radiation has passed through the measurement chamber;
wherein the transmitter and the receiver are part of the wall of the measurement chamber so that the unit is configured for introduction into a matrix, the matrix being a fluid matrix or a fluid-containing matrix;
wherein the measurement chamber is formed by an oblong housing composed of porous material comprising ceramic, silicon, plastic, glass, or metal;
wherein the wall of the measurement chamber is better diffusion-permeable for a first substance of the matrix, at least in certain sections, than for remaining substances of the matrix, in order to balance out concentration differences of the first substance between the measurement medium and the matrix, and thus to separate the first substance from the remaining substances of the matrix;
providing a control and evaluation circuit connected to the transmitter to turn the transmitter on and connected to the receiver to read out a signal from the receiver, the control and evaluation circuit determining the concentration of the first substance in the matrix from a receiver signal; and
applying a coating on at least one of an inside and an outside of the porous material, the coating imparting specific diffusion properties for the first substance relative to the wall.

19. The production method according to claim 18, wherein the coating is applied using a sol-gel method, a vapor deposition method, or a deposition method.

20. The production method according to claim 18, wherein the oblong housing has a first face side, a second face opposite the first face side, and two grooves connecting the first and second face sides on an outside of the oblong housing, and
wherein conductor strips are formed in the two grooves using thick-layer technology.

21. The production method according to claim 18, wherein the oblong housing has a first face side and a second face side opposite to the first face side,
wherein the transmitter and the receiver are attached to the oblong housing on the first and second face sides, respectively, and
wherein the measurement chamber is filled with measurement medium in that the unit is placed into an evacuated chamber and the measurement medium is let into the evacuated chamber.

* * * * *